US008470536B2

(12) United States Patent
Birnboim et al.

(10) Patent No.: US 8,470,536 B2
(45) Date of Patent: Jun. 25, 2013

(54) COMPOSITIONS AND METHOD FOR STORAGE OF NUCLEIC ACID FROM BODILY FLUIDS

(75) Inventors: H. Chaim Birnboim, Ottawa (CA); Adele Jackson, Stittsville (CA); Rafal Iwasiow, Ottawa (CA); Joanne Chartier, White Lake (CA); Paul Lem, Ottawa (CA)

(73) Assignee: DNA Genotek Inc., Ottawa, Ontario (CA)

( * ) Notice: Subject to any disclaimer, the term of this patent is extended or adjusted under 35 U.S.C. 154(b) by 112 days.

(21) Appl. No.: 12/793,048

(22) Filed: Jun. 3, 2010

(65) Prior Publication Data

US 2011/0014658 A1 Jan. 20, 2011

Related U.S. Application Data

(63) Continuation of application No. 11/886,360, filed as application No. PCT/CA2006/000380 on Mar. 14, 2006.

(60) Provisional application No. 60/662,510, filed on Mar. 16, 2005.

(51) Int. Cl.
*C12Q 1/68* (2006.01)
*C12P 19/34* (2006.01)

(52) U.S. Cl.
USPC ............................ 435/6.12; 435/6.1; 435/6.11

(58) Field of Classification Search
None
See application file for complete search history.

(56) References Cited

U.S. PATENT DOCUMENTS

| | | | |
|---|---|---|---|
| 5,140,043 A | 8/1992 | Darr et al. | |
| 5,364,763 A | 11/1994 | Kacian | |
| 5,496,562 A | 3/1996 | Burgoyne | |
| 5,807,527 A | 9/1998 | Burgoyne | |
| 5,814,442 A | 9/1998 | Natarajan et al. | |
| 5,817,630 A | 10/1998 | Hofmann et al. | |
| 5,843,654 A | 12/1998 | Heisler et al. | |
| 6,176,836 B1 | 1/2001 | Trudil et al. | |
| 6,242,188 B1 | 6/2001 | Dattagupta et al. | |
| 6,291,178 B1 | 9/2001 | Schneider | |
| 6,309,827 B1 | 10/2001 | Goldstein et al. | |
| 6,503,716 B1 | 1/2003 | Lai et al. | |
| 6,551,777 B1 | 4/2003 | Shuber et al. | |
| 6,617,170 B2 | 9/2003 | Augello et al. | |
| 6,716,392 B1 | 4/2004 | Putcha et al. | |
| 6,869,769 B2 | 3/2005 | Burgoyne | |
| 7,482,116 B2 | 1/2009 | Birnboim | |
| 7,521,213 B2 | 4/2009 | Hantash | |
| 7,638,307 B2 | 12/2009 | Hantash | |
| 2001/0008614 A1 | 7/2001 | Aronowitz | |
| 2002/0026046 A1 | 2/2002 | Pasloske et al. | |
| 2002/0081575 A1 | 6/2002 | Small et al. | |
| 2004/0038269 A1 | 2/2004 | Birnboim | |
| 2004/0229264 A1 | 11/2004 | Crossman et al. | |

FOREIGN PATENT DOCUMENTS

| | | |
|---|---|---|
| CA | 2072331 | 9/1999 |
| CA | 2236240 | 10/1999 |
| EP | 0586024 | 3/1994 |
| EP | 0734684 | 10/1996 |
| EP | 1207208 | 5/2002 |
| WO | WO 89/06704 | 7/1989 |
| WO | WO 91/02740 | 3/1991 |
| WO | WO 97/05248 | 2/1997 |
| WO | 98/44158 | 10/1998 |
| WO | WO 98/44158 | 10/1998 |
| WO | WO 99/29904 | 6/1999 |
| WO | WO 01/34844 | 5/2001 |
| WO | WO 01/60517 | 8/2001 |
| WO | WO 02/44691 | 6/2002 |
| WO | 03/104251 A2 | 12/2003 |
| WO | 03104251 A2 | 12/2003 |
| WO | WO 03/104251 | 12/2003 |

OTHER PUBLICATIONS

Goldenberger et al., "Simple 'universal DNA extraction procedure compatible with direct PCR amplification," Experientia, 1996, vol. 52, p. 295.*
Birnboim, "Effect of Lipophilic Chelators on Oxyradical-Induced DNA Strand Breaks in Human Granulocytes: Paradoxical Effect of 1,10-Phenanthroline," *Archives of Biochemistry and Biophysics* 294:17-21, 1992.
Birnboim, "Extraction of High Molecular Weight RNA and DNA from Cultured Mammalian Cells," *Methods in Enzymology* 216:154-160, 1993.
Birnboim et al., "A Rapid Alkaline Extraction Procedure for Screening Recombinant Plasmid DNA," Nucleic Acids Research 7:1513-1523, 1979.
Birnboim et al., "Fluorometric Method for Rapid Detection of DNA Strand Breaks in Human White Blood Cells Produced by Low Doses of Radiation," *Cancer Research* 41:1889-1892, 1981.
French et al., "Ultra-Rapid DNA Analysis Using HyBeacon™ Probes and Direct PCR Amplification From Saliva," *Mol. Cell. Probes* 16:319-326, 2002.
Garcia-Closas et al., "Collection of Genomic DNA From Adults in Epidemiological Studies by Buccal Cytobrush and Mouthwash," *Cancer Epidemiology, Biomarkers & Prevention* 10:687-696, 2001.
Heath et al. "Use of Buccal Cells Collected in Mouthwash as a Source of DNA for Clinical Testing," *Arch. Pathol. Lab. Med.* 125:127-133, 2001.
Hirade et al., "Speciation of Iron in River Water," *Analytical Sciences* 4:605-609, 1988.

(Continued)

*Primary Examiner* — Young J Kim
(74) *Attorney, Agent, or Firm* — Clark & Elbing LLP; Kristina Bieker-Brady (57) ABSTRACT

The present invention provides an aqueous composition and method for extracting nucleic acid from a sample of bodily fluid, such as saliva, such that the nucleic acid within said sample remains stable for at least fourteen days at room temperature. The composition permits direct use of the extracted and stored DNA in an amplification reaction without further processing.

13 Claims, 6 Drawing Sheets

OTHER PUBLICATIONS

Loens et al., "Detection of *Mycoplasma Pneumoniae* in Spiked Clinical Samples by Nucleic Acid Sequence-Based Amplification," *J. Clinical Microbiology* 40:1339-1345, 2002.

Lum and Marchand, "A Simple Mouthwash Method for Obtaining Genomic DNA in Molecular Epidemiological Studies," *Cancer Epidemiology, Biomarkers & Prevention* 7:719-724, 1998.

Nilsson et al., "Real-Time Monitoring of DNA Manipulators Using Biosensor Technology," *Analytical Biochemistry* 224:400-408, 1995.

Roberts et al., "UV Laser Machined Polymer Substrates for the Development of Microdiagnostic Systems," *Analytical Chemistry* 69:2035-2042, 1997.

Rymaszewski et al., "Estimation of Cellular DNA Content in Cell Lysates Suitable for RNA Isolation," *Analytical Biochem.* 188:91-96, 1990.

Schmitteckert et al., "DNA Detection in Hair of Transgenic Mice—A Simple Technique Minimizing the Distress on the Animals," *Laboratory Animals* 33(4):385-389, 1999.

Seutin et al., "Preservation of Avian Blood and Tissue Samples for DNA Analyses," *Can. J. Zool.* 69:82-90, 1991.

Terasaki et al., "Saliva as DNA Source for HLA Typing," *Human Immunology* 59:597-598, 1998.

van Schie and Wilson, "Salvia: A Convenient Source of DNA for Analysis of Bi-Allelic Polymorphisms of Fcγ Receptor IIA (CD32) and Fcγ Receptor IIIB (CD16)," *Journal Immunological Methods* 208:91-101, 1997.

Videira et al., "Assembly Kinetics and Identification of Precursor Proteins of Complex I from *Neurospora crassa*," *European Journal of Biochemistry* 181:493-502, 1989.

Applicant's Letter in Response to the Written Opinion, dated Jan. 16, 2007.

International Search Report for PCT/CA03/00869, mailed Mar. 30, 2004.

International Search Report for PCT/CA06/000380, mailed Jul. 6, 2006.

Written Opinion for PCT/CA06/000380, mailed Jul. 6, 2006.

Supplementary European Search Report for European Patent Application No. EP 06 72 1659, dated Apr. 24, 2009.

Japanese Office Action and its translation of corresponding Application No. JP2008-501124; Apr. 24, 2012; Hideo Nomura.

Office Action for Australian Patent Application No. 2006225044 dated Dec. 23, 2010.

Office Action for Australian Patent Application No. 2006225044 dated Jan. 18, 2012.

Office Action for Chinese Patent No. CN 200680016802.5 dated Jan. 30, 2012 (English Language Translation Only).

Office Action for Chinese Patent No. CN 200680016802.5 dated Jul. 31, 2012 (English Language Translation Provided).

Communication Pursuant to Article 94(3) EPC for European Patent Application No. 06 721 659.8-2402 dated Jun. 27, 2011.

Office Action for Japanese Patent Application No. 2008-501124 dated Aug. 19, 2011 (English Language Translation Provided).

Office Action for Israeli Patent Application No. 185955 dated Jun. 20, 2011 (English Language Translation Only).

Office Action for U.S. Appl. No. 11/886,360 dated Feb. 23, 2011.

Office Action for Israeli Patent Application No. 185955 dated Sep. 12, 2012 (English Translation).

English Translation of Dismissal of Amendment in Japanese Patent Application No. 2008501124 issued Mar. 12, 2013.

English Translation of Decision of Rejection in Japanese Patent Application No. 2008501124 issued Mar. 13, 2013.

\* cited by examiner

FIGURE 1

Day 1

Day 7

Day 14

Day 21

FIGURE 2

Day 365

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
atgcttagta ggcaattctg                20

<210> SEQ ID NO 2
<211> LENGTH: 18
<212> TYPE: DNA
<213> ORGANISM: Artificial Sequence
<220> FEATURE:
<223> OTHER INFORMATION: Synthetic Construct

<400> SEQUENCE: 2
tttggttgtc agcagagg                18

```
<210> SEQ ID NO 3
<211> LENGTH: 17
<212> TYPE: DNA
<213> ORGANISM: Artificial Sequence
<220> FEATURE:
<223> OTHER INFORMATION: Synthetic Construct

<400> SEQUENCE: 3
gccctctgcc agttcta                                                  17

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct

<400> SEQUENCE: 4
ttcaggcccg tgatgt                                                   16
```

COMPOSITIONS AND METHOD FOR STORAGE OF NUCLEIC ACID FROM BODILY FLUIDS

This application is a continuation of, and claims priority from, U.S. patent application Ser. No. 11/886,360, filed Mar. 28, 2008, which claims priority under 35 U.S.C. §371 from international application PCT/CA2006/000380, filed Mar. 14, 2006, which claims the benefit of the filing date of U.S. Provisional Patent Application Ser. No. 60/662,510, filed Mar. 16, 2005, the disclosures of which are incorporated by reference in their entirety.

This application contains a sequence listing in computer readable form titled 1122638 Sequence Listing, created Sep. 9, 2010 and a size of 961 bytes, which is incorporated herein by reference.

FIELD OF THE INVENTION

The field of the invention generally relates to compositions and methods for isolation and storage of nucleic acids from bodily fluids, such as saliva, for detection of nucleotide sequences. More specifically, the invention relates to compositions and methods that do not require a separate step for extraction of nucleic acids prior to use in nucleic acid amplification reactions.

BACKGROUND

Molecular-based techniques involving the amplification of nucleic acids are increasingly being used in forensics, law enforcement, the military, human medicine, veterinary medicine, and research. In forensic, military and mass disaster situations, for example, DNA samples are now routinely taken from living persons thought to be relatives of unidentified victims of accident or foul play, to aid in identification of the dead. Military personnel or other individuals who expect to encounter hazardous situations where their lives may be at risk may wish to store DNA samples prior to exposing themselves to these hazards. In the law enforcement area, convicted felons in both Canada and the United States are now required to provide DNA samples. The use of DNA-based tests is expected to increase in medicine, for example, in testing for cystic fibrosis, cytochrome P450 isotypes, polymorphisms affecting susceptibility to infectious and autoimmune diseases, HLA typing, paternity issues, to name but a few. In clinical studies, an example would be to screen populations for colon cancer-predisposing genes or family members of a breast cancer victim for breast cancer predisposing genes. One technique for the amplification of DNA is the polymerase chain reaction (PCR).

PCR is a rapid, inexpensive and relatively simple means of amplifying copies of DNA molecules from a variety of source materials. However, a limitation of PCR is that DNA source materials typically contain a variety of inhibitors, such as pigments, proteins, saccharides and/or other impurities that interfere with the amplification reaction. For example, a variety of DNA polymerases, including Taq DNA polymerase (a typical thermostable DNA polymerase derived from *Thermus aquaticus*) are known to be inhibited by traces of body fluid-derived impurities in a PCR mixture. To overcome the problem of inhibitors within the DNA source material, there is typically a requirement for the purification of the DNA from the source material prior to amplification. However, purification procedures often involve multiple steps that can be time-consuming and expensive.

DNA can be extracted from nearly every type of cell in the human body and from a variety of cell-containing bodily fluids. The term "bodily fluid", as used herein, can refers to a naturally occurring fluid from an animal, such as saliva, sputum, serum, plasma, blood, urine, mucus, gastric juices, pancreatic juices, semen, products of lactation or menstruation, tears, or lymph. A typical source of bodily fluid for extraction of DNA is white blood cells in venous blood. However, the use of blood as a source of DNA has many disadvantages. Collection of blood is not a trivial procedure. Taking of venous blood requires trained personnel. Furthermore, it is an invasive procedure, which frequently causes a degree of distress and pain to the donor. Precautions are needed to minimize exposure of blood collecting personnel to blood-borne pathogens. Once collected, the blood sample must be either frozen or quickly transported to a laboratory for extraction of DNA. A simpler procedure for obtaining blood is to collect a few drops after a finger prick and blotting it onto a piece of filter paper. Less training of personnel is required. Once dried, the DNA is quite stable. The amount of DNA recovered is small but sufficient for many forensic purposes. However, a finger prick is still an invasive procedure and haeme derived from haemoglobin in red blood cells can inhibit some types of DNA analysis.

Swabbing the inside of the cheek with a brush (a buccal swab) is another method of obtaining cells that contain DNA. This procedure is much less invasive than taking blood and permits collection by individuals with less training than is required in the collection of blood. Once collected, the time that usable DNA can be recovered is relatively short. Microbes in the mouth can degrade the DNA. However, this time can be extended by either drying the swab or wiping it onto filter paper and drying it.

Saliva is a fairly clear, colorless fluid secreted principally by the major salivary glands (parotid, submandibular, and sublingual). Its function is to lubricate and cleanse the oral cavity, as well as to initiate the process of digestion. The parotid gland primarily secretes serous (watery) saliva, while the other glands secrete a mixture of serous and mucinous (sticky) saliva. Components of saliva include mucins, and digestive enzymes.

Mucins are high molecular weight glycosylated proteins that form a major part of a protective biofilm on the surface of epithelial cells, where they can provide a barrier to particulate matter and bind microorganisms. These glycoproteins contribute greatly to the viscous nature of saliva.

It has long been known that cellular DNA is present in saliva and that this DNA is suitable for forensic purposes. Forensic use is typically limited to victim or suspect identification, using the small amounts of DNA from saliva that may recovered at a crime scene or from the back of a postage stamp. The notion that saliva may be a reliable source of genomic DNA and a rival to venous blood samples for this purpose has been investigated by van Schie, et al. (van Schie et al., (1997) *J. Immunol. Methods.* 208: 91-101). van Schie et al. used freshly collected or frozen saliva samples and purified the DNA by a fairly complex extraction procedure. Estimates of the quantity of DNA recovered were based upon light absorption at 260 nm, a procedure known to be an unreliable method since other common biological macromolecules, such as RNA, have essentially the same ultraviolet light absorption spectrum. Nevertheless, these authors showed that quality genomic DNA was indeed present by gel electrophoretic analysis and polymerase chain reaction analysis for certain allelic polymorphisms. Terasaki et al. (Terasaki et al. (1998) *Hum Immunol.* 59: 597-598) reported similar results about the suitability of saliva as a source of DNA for HLA typing by polymerase chain reaction analysis. Although the amount of DNA recovered was reported, the method used to measure DNA was not. These authors provided 3 examples where saliva dried on filter paper yielded DNA suitable for analysis.

There are significant advantages to providing a saliva sample rather than a blood sample as a source of DNA. Donors generally prefer donating saliva rather than blood because of the discomfort, pain, or apprehension associated with phlebotomy or pin-pricks. Saliva has a further advantage of not requiring specialized personnel thereby reducing cost where mass sample collection is being carried out. However, it will be clear to the skilled worker that while saliva is a preferred source of DNA, other bodily fluids, including blood, can be used.

More recently, it has been discovered that saliva can be used directly for real-time PCR without any DNA purification procedure. French et al. (French et al. (2002) Molecular And Cellular Probes. 16: 319-326) diluted fresh whole saliva 1:1 with water and used this mixture immediately, or following storage at 4° C. (2-3 days) or −20° C., for real-time PCR with a LightCycler instrument (Roche Diagnostics). PCR reaction volumes were typically 20 µl, containing 2 µl of saliva (diluted to 50% in water). The calculated concentration of DNA available for PCR was found to be between 0.1 ng/µl and 3.5 ng/µl, varying between samples obtained from different individuals and on different days. The authors commented that the amount of DNA available for amplification in crude saliva may not account for all of the DNA present in saliva samples, where a quantity of the total DNA may still reside within buccal cells or be too degraded to permit target amplification. A significant reduction in assay efficiency was not observed with saliva samples stored at 4° C. (2-3 days) or −20° C.

With the increasing use of DNA-based analysis in forensics, law enforcement, military, human medicine, veterinary medicine, and research, there is a need for compositions and methods that allow bodily fluids such as saliva to become a standard reliable source of DNA from an individual (to replace blood, the current standard). Desirably, it would be possible to use such compositions and methods for detecting DNA without requiring a separate step for extraction and purification of DNA from the saliva. Furthermore, it would be desirable to be able to store the bodily fluid at ambient temperature for several days. This would be especially advantageous when shipping of the saliva sample is required and/or a source of refrigeration is not available. In addition, it would be desirable if the concentration of genomic DNA in the saliva sample was high enough for both traditional PCR and real-time PCR without requiring additional steps. Traditional PCR usually requires DNA template in amounts>10 ng. According to the Roche Molecular Biochemicals PCR Application Manual ($2^{nd}$ edition, 1999, Roche Diagnostics), traditional PCR with low amounts of template (<10 ng human genomic DNA) requires special reaction modifications, such as changes in cycle number, redesign of primers, use of "Hot Start", etc. In contrast, real-time PCR is much more sensitive than traditional PCR. For example, the LightCycler real-time PCR instrument (Roche Diagnostics) has 100% sensitivity for detecting 30 pg of control human genomic DNA (Light-Cycler Control Kit DNA manual, version 3, 2003).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a composition and method for storage of DNA from a bodily fluid such as saliva, that permits direct use of the DNA sample in a nucleic acid amplification reaction.

In accordance with one aspect of the invention, there is provided an aqueous composition for extracting nucleic acid from a sample of a bodily fluid such that said nucleic within said sample remains stable for at least 14 days at room temperature, wherein said composition does not inhibit nucleic acid amplification when said composition is added to an amplification reaction mixture at an amount of at least 2% of the total volume of said amplification reaction mixture.

In accordance with another aspect of the invention, there is provided a method of amplifying DNA directly from a bodily fluid, comprising: (a) mixing a sample of the bodily fluid with an equal volume of an aqueous composition according to the present invention; (b) subjecting a portion of the mixture formed in step (a) to PCR amplification.

In accordance with another aspect of the invention, there is provided a kit for amplifying DNA from a bodily fluid, comprising: (a) an aqueous composition according to the present invention; and (b) instructions for the use thereof.

The chelating agent of the composition can be selected from the group consisting of: ethylenediamine tetraacetic acid (EDTA), cyclohexane diaminetetraacetate (CDTA), diethylenetriamine pentaacetic acid (DTPA), tetraazacyclododecanetetraacetic acid (DOTA), tetraazacyclotetradecanetetraacetic acid (TETA), and desferrioximine, or chelator analogs thereof. For CDTA, concentrations in the 1-20 mM range are sufficient, however other concentrations would work, and the compositions of the invention are not intended to be limited to this range.

The denaturing agent of the composition can be selected from the group consisting of: urea, dodecyl sulfate, guanidinium chloride, guanidinium thiocyanate, perchlorate, and an alcohol. Desirably, the denaturing agent is urea, dodecyl sulfate, or an alcohol, wherein the alcohol is 10%-60% of the total composition volume. The alcohols can be methanol, ethanol, n-propanol, isopropanol, n-butanol, trifluoroethanol, phenol, or 2,6-di-tert-butyl-4-methylphenol.

In another embodiment, the composition also includes a reducing agent. For example, it can include one or more of the following: ascorbic acid, dithionite, erythiorbate, N-acetylcysteine, cysteine, glutathione, dithiothreitol, 2-mercaptoethanol, dierythritol, a resin-supported thiol, a resin-supported phosphine, vitamin E, and trolox, or salts thereof.

The pH of the composition can between from about 5.0 and about 11.0, desirably from about 6.5 to about 7.5, and most desirably, about 7.0. For the preservation of DNA, a pH from about 7.0 to about 10.0 can be used. Depending on other components of the compositions, desirable pHs are about 7.5, about 8.0, or a pH range from about 8.0 to about 9.0. A buffer, such as HEPES, TRIS, or carbonate buffer can be added to the composition to maintain the pH in a constant range. For the preservation of RNA, a pH from about 5.0 to about 7.0, desirably from about 6.5 to about 6.8 can be used. Again, a buffer, such as BES, can be used to maintain the pH in a constant range.

BRIEF DESCRIPTION OF THE FIGURES

| Lane # | Description |
| --- | --- |
| 1 | 100-bp marker |
| 2 | Day 1 |
| 3 | Day 14 |
| 4 | Day 365 |
| 5 | 100-bp marker |

| Lane # | Description |
| --- | --- |
| 1 | 100-bp marker |
| 2 | Water |
| 3 | 100 mM sodium hydroxide |
| 4 | 100 mM potassium hydroxide |
| 5 | 200 mM sodium carbonate |
| 6 | 100-bp marker |

| Lane # | Final concentration of NaOH (mM) |
| --- | --- |
| 1 | 100-bp marker |
| 2 | 0 |
| 3 | 1 |
| 4 | 2 |
| 5 | 4 |
| 6 | 6 |
| 7 | 8 |
| 8 | 10 |
| 9 | 12 |
| 10 | 14 |
| 11 | 100-bp marker |

| Lane # | Volume of NaOH plus saliva (μL) |
| --- | --- |
| 1 | 100-bp marker |
| 2 | 0 |
| 3 | 1 |
| 4 | 2 |
| 5 | 3 |
| 6 | 4 |
| 7 | 5 |
| 8 | 6 |
| 9 | 7 |
| 10 | 8 |
| 11 | 9 |
| 12 | 10 |
| 13 | 12 |
| 14 | 14 |
| 15 | 16 |
| 16 | 18 |
| 17 | 20 |
| 18 | 100-bp marker |

| Lane # | Description |
| --- | --- |
| 1 | 100-bp marker |
| 2 | Water |
| 3 | 100 mM sodium hydroxide |
| 4 | 100 mM potassium hydroxide |
| 5 | 200 mM sodium carbonate |
| 6 | Oragene solution |
| 7 | 100-bp marker |

DETAILED DESCRIPTION OF THE INVENTION

As will be described in more detail below, the present invention relates to aqueous compositions and methods for extraction and storage of DNA from bodily fluids such as saliva, wherein the DNA in the resulting composition remains stable for at least fourteen days at room temperature. The composition of the present invention permits DNA released from saliva, or other bodily fluid, to be used directly in nucleic acid amplification reactions without any additional processing steps.

The term "about", as used herein, refers to +/−10% of the stated value of a chemical or obvious equivalent thereof.

The term "bodily fluid", as used herein, refers to a naturally occurring fluid from an animal, such as saliva, sputum, serum, plasma, blood, urine, mucus, gastric juices, pancreatic juices, semen, products of lactation or menstruation, tears, or lymph.

The term "mucin", as used herein, refers to any mucoprotein that raises the viscosity of the medium surrounding the cells that secrete it.

The term "mucoid", as used herein, refers to any bodily fluid containing mucin.

The term "nucleic acid", as used herein, refers to a chain of nucleotides, including deoxyribonucleic acid (DNA) or ribonucleic acid (RNA), typically found in nature in chromosomes, chromatin, mitochondria, cytoplasm, ribosomes, bacteria, fungi and/or viruses.

The term "DNA polymerase", as used herein, refers to an enzyme that catalyzes a deoxyribonucleic acid synthesis via a primer binding and subsequent incorporation of nucleotides. Suitable polymerases include, but are not limited to, DNA polymerase I derived from *E. coli*, the Klenow fragment of DNA polymerase derived from *E. coli*, T4 DNA polymerase, Taq DNA polymerase, *T. litoralis* DNA polymerase, Tth DNA polymerase and Pfu DNA polymerase.

The term "primer", as used herein, refers to an oligonucleotide acting as a starting point from which the synthesis begins in the presence of a DNA template, reagents for polymerization and so on. Although a primer is preferably single-stranded, double-stranded primers may also be used. When double-stranded primers are used, it is desirable to convert them into their single-stranded forms before use in an amplification reaction. A primer may be synthesized using well known methods, or may be isolated from an organism.

The term "saliva", as used herein, refers to the secretion, or combination of secretions, from any of the salivary glands, including the parotid, submaxillary, and sublingual glands, optionally mixed with the secretions from the numerous small labial, buccal, and palatal glands that line the mouth.

The term "sputum", as used herein, refers to mucoid matter contained in or discharged from the nasal or buccal cavity of a mammal, including saliva and discharges from the respiratory passages, including the lungs.

The term "stable", as used herein to describe nucleic acid within a saliva sample, refers to the ability of that nucleic acid to support PCR amplification into a detectable product. For example, nucleic acid within a sample of saliva is said to remain stable for at least fourteen days if a PCR product is obtainable at least fourteen days after being mixed with the aqueous composition of the present invention.

The term "subject", as used herein, refers to an animal or human. Desirably, the subject is a mammal that can produce saliva for the purposes of nucleic acid detection. Most desirably, the subject is human.

Composition

The composition of the present invention is for extracting nucleic acid from a bodily fluid and maintaining the nucleic acid contained therein stable for at least fourteen days at room temperature. In a preferred embodiment, the bodily fluid is saliva. The composition of the present invention further permits direct use of the extracted nucleic acid in an amplification reaction without further processing of the nucleic acid-containing composition. In particular, the components of the composition are at a concentration sufficiently low to permit nucleic acid amplification when a portion that constitutes at least 2% of the total reaction volume is added to an amplification reaction. The term "processing" as used herein refers to mechanical or chemical steps used to isolate or purify nucleic acid from a storage composition.

Selection of the specific components of the composition is made based on various criteria, including, for example, cost, availability, downstream application, and safety. As would be readily appreciated by a worker skilled in the art, the concentration of the components is sufficiently high to stabilize the bodily fluid-derived nucleic acid for at least fourteen days at room temperature, while not interfering with the direct use of a portion of the nucleic acid-containing composition in an amplification reaction. For example, when a sample of saliva is mixed 1:1 (v/v) with the composition of the present invention, no inhibition of nucleic acid amplification is observed when the composition consists of 100 mM NaOH in water and an amount of the composition/bodily fluid is added to the amplification reaction such that it constitutes from 20% of the total reaction volume (i.e., the composition of the present invention constitutes from 2% to 20% of the total volume).

A major cause of nucleic acid instability in biological samples is the presence of deoxyribonucleases and ribonucleases. Deoxyribonucleases and ribonucleases are enzymes that break down DNA or RNA, respectively. Their main source in the digestive tract is secretions of the pancreas, although lower levels may be present in saliva and in cells of the salivary gland and buccal mucosa. In addition, microorganisms resident in the mouth or from recently ingested foods may release deoxyribonucleases or ribonucleases. Over time, the nucleic acid within a sample of saliva stored in water would be expected to degrade or break down into smaller fragments.

Desirably, the composition provides inhibition of nucleases, including deoxyribonucleases, and chemical stabilization of nucleic acids. Nuclease inhibition is achieved through the use of denaturing agents, proteases and/or heating. Chemical stabilization of the nucleic acids in saliva sample is achieved through the use of pH buffers to maintain an appropriate pH, and/or the use of chelating agents to prevent the phenomenon of metal redox cycling or the binding of metal ions to the phosphate backbone of nucleic acids.

The action of deoxyribonucleases and ribonucleases can be inhibited by denaturing agents that destroy the complex structures of these enzymes (proteins). Hence, denaturing agents can be included in the composition of the present invention. A non-limiting example of a suitable denaturing agent is sodium dodecyl sulfate (SDS).

Low specificity proteases, such as proteinase K, are frequently used to digest proteins. In one embodiment of the present invention, a protease is added to the composition before, after or at the time of mixing with saliva. Since the proteases are themselves proteins, their action can be inhibited by denaturing agents. Thus, a balance must be struck between the concentration of the denaturing agents that will, on the one hand, inhibit deoxyribonucleases or ribonucleases and denature other proteins in saliva and, on the other hand, not significantly inhibit the proteolytic enzymes.

The method of the present invention optionally includes the step of heating the saliva-containing mixture. Heating of saliva samples (in the range 45 to 90° C.) can act as a 'reversible' denaturing agent, particularly when used in combination with denaturing agents. That is, it has been found that a lower concentration of a chemical denaturing agent may be used if combined with the denaturing action of heat. Optionally, a heating step is included in the method of the present invention prior to the amplification step in order to improve the release of DNA and improve the yield of the amplification reaction. It should be appreciated that this optional heating step does not constitute a "processing" step for isolation or purification of the nucleic acid with the sample.

DNA has a strong affinity for metal ions, some of which, such as the common transition metals iron or copper, can catalyze the formation of reactive oxygen species. Therefore, one embodiment of the present invention provides a composition comprising one or more chelators that can form complexes with metal ions to prevent them from binding to DNA, remove metal ions that have already bound to DNA, or bind metal ions strongly enough to inhibit their redox cycling, and hence, the formation of reactive oxygen species. The amount or concentration of chelator will depend upon the strength of the chelator, which would need to be determined empirically. Cyclohexanediamine tetraacetate (CDTA) is a commonly used chelator. In a specific example, 20 mM CDTA is used; however, the skilled worker would appreciate and readily determine other concentrations of CDTA that would be appropriate.

The chemical backbone and the purine bases of DNA are understood to be most stable at slightly alkaline pH, with an optimal stability generally recognized as being within a pH range of about 7-11, and desirably at a pH of about 8. Below a pH of about 6, depurination (i.e., spontaneous loss of purine bases from the deoxyriboside phosphate backbone) can occur. Above a pH of about 10, spontaneous loss of amino groups from cytosine may occur, thereby converting cytosine to uracil. Above a pH of about 12, DNA is denatured, converting it from the double-strand form to the single-strand form. In contrast, RNA is most stable in the pH range of 5.0 to 7.0, desirably a pH of from 6.5 to 6.8. Accordingly, in one embodiment of the present invention, the pH of the composition is maintained by including a buffering agent, desirably those that best control the pH within the range of about 5 to 11. One non-limiting example of a suitable buffering agent in the pH range 6.5 to 9.5 is Tris hydrochloride.

In accordance with one embodiment of the present invention, the composition comprises a denaturing agent and optionally proteinase K, a chelator and a pH buffer to maintain the pH within the range of 7-11.

In accordance with an alternative embodiment of the present invention, the composition does not contain a denaturing agent, a proteinase K, a chelator or a pH buffer. Rather, inhibition of nucleases and extraction and storage of DNA is achieved by maintaining a basic pH.

Surprisingly, it has been found that a mixture of a bodily fluid, such as saliva, with an aqueous composition containing a basic agent, for example, an alkali metal hydroxide, a soluble alkaline earth metal hydroxide, an alkali metal oxide or an organic base can release DNA from the bodily fluid such that the released DNA can function as a template in a PCR reaction. While not wishing to be bound by theory, it is believed the composition achieves denaturation of proteins, inhibition of nucleases and extraction and storage of DNA by maintaining a basic pH. In selecting the appropriate base it is understood that a base containing a metal that is reactive with DNA, or that would interfere with the DNA polymerase employed in the amplification reaction, would not be suitable for use in the composition of the present invention.

In accordance with a specific embodiment of the present invention, the composition for use in extracting and storing DNA from saliva is a sodium hydroxide (NaOH) solution containing from 50 mM to 400 mM.

As noted above, in order to be used directly in an amplification reaction, it is necessary to ensure that the concentration of the various components of the composition of the present invention are such that they do not inhibit the amplification reaction. One example of a method for determining the interference of a component on an amplification reaction is the inclusion of graded concentrations of the composition within the amplification reaction to determine the maximum amount of composition that can be added to the reaction without inhibiting the reaction. A second example of such a methodology includes first combining the composition and the saliva, then including graded volumes of the saliva/composition mixture within the PCR amplification reaction to determine the maximum amount of the saliva/composition mixture to be added to the reaction without inhibiting the reaction.

Once a determination is made as to the amount of a component that can be tolerated in a PCR, or other amplification reaction, that information is used to calculate the amount to be included in the composition of the present invention.

Method

In accordance with another aspect of the present invention, there is provided a method for storing and amplifying a nucleic acid sample derived from saliva. The method comprises the steps of mixing a sample of saliva with the composition of the present invention, subsequently mixing an aliquot of the resulting saliva-containing mixture with an amplification reaction mixture and amplifying the nucleic acid within the aliquot of the saliva-containing mixture.

To collect saliva from a subject it is preferred that the mouth be rinsed before sampling. Food particles can introduce foreign DNA and saliva transferred by kissing can be a source of foreign human DNA. The mouth can be rinsed with about 50 ml of tepid water by vigorous swishing or by brushing with a toothbrush without toothpaste. Unstimulated saliva is usually of the mucinous type and is secreted at a slow rate. Stimulated saliva (anticipation of tasty food, sweet or sour candy) is of the serous (watery) type and secreted at a faster rate. It has been found that there is more DNA in 2 ml of unstimulated saliva than in 2 ml of stimulated saliva. After rinsing of the mouth and waiting about two or three minutes for the mouth to clear of water, the donor may spit a volume (for example, about 1 ml) of "unstimulated" saliva into the receiving tube. If this proves to be difficult, saliva flow can conveniently be stimulated with a few grains of table sugar, or any other such saliva-stimulatory substance that does not interfere with DNA stability or subsequent amplification.

The method of the present invention optionally includes the step of heating the saliva-containing mixture. Heating of saliva samples (in the range 45 to 90° C.) can act as a 'reversible' denaturing agent, particularly when used in combination with denaturing agents. That is, it has been found that a lower concentration of a chemical denaturing agent may be used if combined with the physical denaturing action of heat. Therefore, an optional heating step is included in the method of the present invention prior to the amplification step in order to improve the release of DNA and improve the yield of the amplification reaction.

Methods of the invention are conveniently practiced by providing the compositions used in such method in the form of a kit. Such a kit preferably contains appropriate solutions, enzymes, salts or detergents (or equivalents thereof). At least one type of positive standard may be provided and can include either nucleic acid (DNA or RNA) template useful in the detection of a target gene or DNA, or primers.

Optionally the kit includes a container, such as that described in International PCT Application No. WO 03/104251, which contains the composition of the present invention and that is suitable for saliva collection.

To gain a better understanding of the invention described herein, the following examples are set forth. It should be understood that these examples are for illustrative purposes only. Therefore, they should not limit the scope of this invention in any way.

EXAMPLES

Example 1

Protocol for Obtaining Saliva Samples from Subjects Capable of Following Instructions The subject is instructed to wait for a period of 30-60 minutes before last eating. The subject will brush his teeth without using toothpaste, if possible. The subject will rinse his/her mouth with 50 ml of cool or tepid water. The subject will be requested to wait for 2 minutes to allow the mouth to clear of water, then spit saliva into the special collection tube until the level of saliva reaches the 1 ml mark. Waiting after last eating and rinsing the mouth is desirable but not essential. Collection of saliva may take several minutes. If the subject finds that he/she is unable to deliver sufficient saliva, he/she will be given a few grains of table sugar to chew, and told not to be concerned if some of the sugar is spit into the tube.

Where two or more samples are to be taken from a donor for purposes of comparing two compositions, the donor is asked to deliver small amounts of saliva alternating between two or more tubes until each tube is filled to the 1 ml mark. This is necessary because the composition of saliva can vary during the process of spitting.

When the required amount of saliva is collected, it is mixed with 1 ml of an aqueous composition. The precise way in which this will be introduced will depend upon the container design. Once the aqueous composition is introduced, the container is securely capped. The DNA-containing sample can be maintained at room temperature for at least fourteen days. A portion of the DNA-containing sample in aqueous solution can be used as a DNA template at any time up to fourteen days for direct addition into a PCR reaction.

Example 2

Stability of DNA in Saliva and PCR Amplification of Saliva-Derived DNA with a Heating Step Method Saliva was collected from a single donor, using the protocol described in Example 1, and individual samples of the saliva were mixed 1:1 with a solution consisting of 20 mM CDTA; 400 mM NaOAc (sodium acetate); 200 mM Tris-HCl, 0.05% SDS (sodium dodecyl sulfate); pH adjusted to 8.0. 20 µL of Proteinase K (1 mg/mL concentration) was then added to this mixture (10 µg/mL final concentration). The samples were vortexed, and then allowed to sit at room temperature (approximately 24° C.). At Day 1, Day 14, and Day 365, 2 µl of the saliva/solution sample was added directly to a standard 50 µl PCR reaction following incubation for 1 hour at 60° C.

PCR Conditions

PCR reactions were performed in an Eppendorf Mastercycler™ gradient PCR machine. The total reaction volume was 50 µL. Each reaction contained Invitrogen PCR Mastermix plus Tris-HCl (pH 8.0, 10 mM final concentration), $MgCl_2$ (2 mM final concentration), each of the 4 dNTPs (400 µM final concentration), 10 pmoles of each PCR primer for a 560 bp fragment of the thymidylate synthase gene (Forward: 5'-ATGCTTAGTAGGCAATTCTG-3' (SEQ ID NO: D, Reverse: 5'-TTTGGTTGTCAGCAGAGG-3' (SEQ ID NO: 2)), and 2 units of Taq DNA polymerase.

Thermocycling conditions consisted of: 1 cycle of 94° C. for 1 min; 30 cycles of 94° C. for 30 sec, 55° C. for 60 sec, 72° C. for 120 sec; 1 cycle of 72° C. for 4 min.

Agarose Gel Electrophoresis

Eight-µl from each PCR reaction was loaded onto a 1% agarose gel. A 100-bp ladder was used as a marker. Following electrophoresis, the agarose gel was stained with ethidium bromide (1 µg/ml, 15 min), and photographed using a UVP Digi Doc-it™ System under transillumination at 300 nm.

Summary

Figure 1:
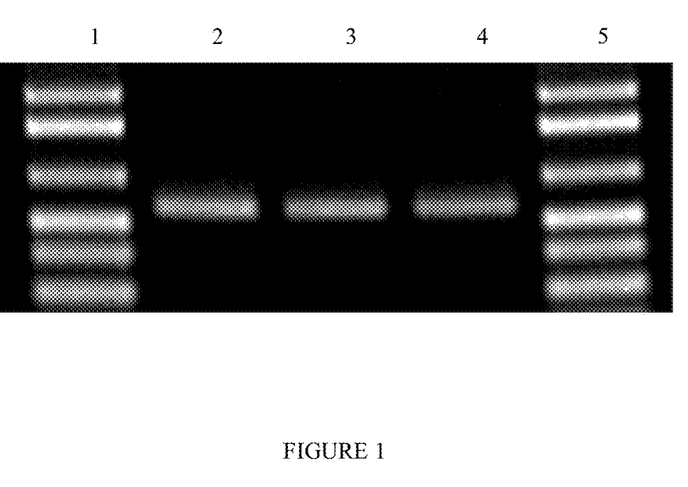
FIG. 1 shows an agarose gel stained with ethidium bromide following electrophoresis of PCR products and depicts direct amplification of DNA from saliva mixed with an aqueous composition and stored at room temperature for one day, fourteen days, or 365 days. Prior to PCR, the samples were incubated at 60° C. for 1 hour. The contents of the lanes in the agarose gel are as follows.

As can been seen in FIG. 1, DNA from saliva was stable when mixed 1:1 with the composition and stored at room temperature for 1, 14, and 365 days.

Example 3

Stability of DNA in Saliva and PCR Amplification of Saliva-Derived DNA

Method

Saliva was collected from a single donor, using the protocol described in Example 1, and individual samples of the saliva were mixed 1:1 with each of the following solutions:

water
100 mM NaOH (sodium hydroxide)
100 mM KOH (potassium hydroxide)
200 mM $Na_2CO_3$ (sodium carbonate)

The samples were vortexed and allowed to sit at room temperature (approximately 24° C.). At Day 1, Day 7, Day 14, Day 21, and Day 365, 2 µl of the saliva/solution sample was added directly to a standard 50 µl PCR reaction.

PCR Conditions

PCR reaction conditions were the same as in Example 2. Thermocycling conditions were the same as in Example 2.

Agarose Gel Electrophoresis

Agarose gel electrophoresis was performed as described in Example 2.

Summary

Figure 2:
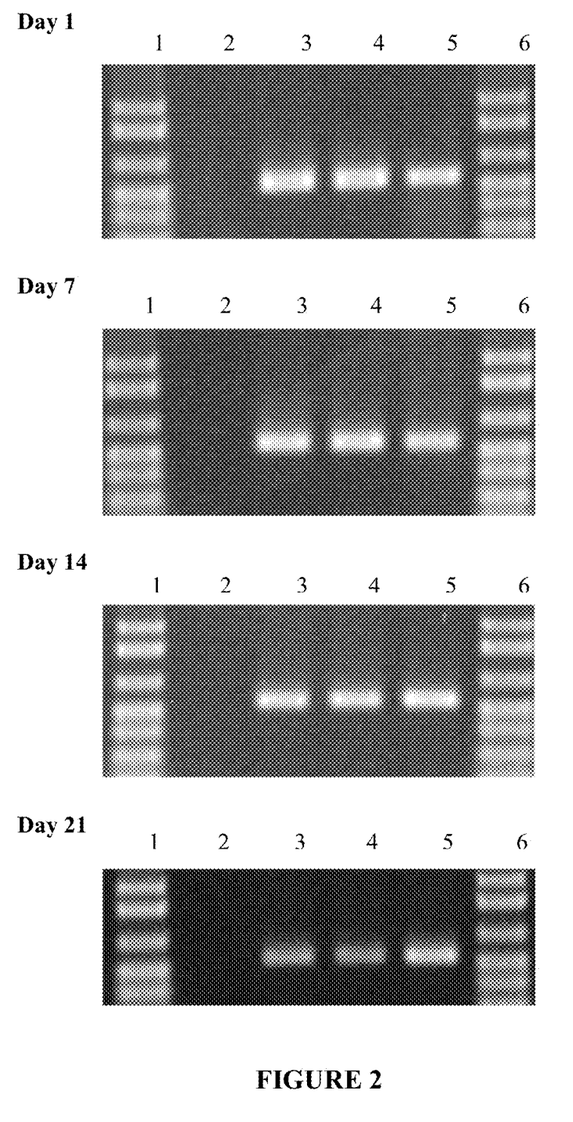
FIG. 2 shows an agarose gel stained with ethidium bromide following electrophoresis of PCR products and depicts direct amplification of DNA from saliva mixed with an equal volume of the aqueous composition shown in the following table following storage at room temperature for 1 day, 7 days, 14 days, 21 days, or 365 days. The contents of the lanes in the agarose gel are as follows.

As can been seen in FIG. 2, DNA from saliva was stable and usable for PCR when mixed 1:1 with 100 mM NaOH, 100 mM KOH and 200 mM $Na_2CO_3$, and stored at room temperature for 1, 7, 14 21, and 365 days.

Example 4

Figure 3:
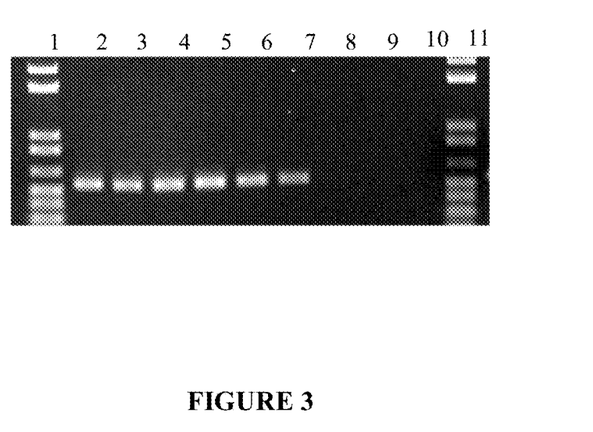
FIG. 3 shows an agarose gel stained with ethidium bromide following electrophoresis of PCR products and depicts the effect of graded concentrations of NaOH on a PCR amplification reaction containing purified human DNA. The contents of the lanes in the agarose gel are as follows.

Determination of the Concentration of Sodium Hydroxide that is Non-Inhibitory in a PCR Reaction Method A series of 9 PCR reaction tubes was set up, with each tube having a different final concentration of NaOH. The final concentration of NaOH ranged from 0 to 14 mM, as indicated in FIG. 3. This is equivalent to a starting concentration of 50 to 400 mM (i.e. 1 ml of 400 mM NaOH plus 1 ml of saliva; then 2 µl of this mixture is used in a 50 µl PCR reaction). To isolate the effect of NaOH, no saliva was added to the reaction tubes.

PCR Conditions

In addition to the NaOH, each reaction contained KCl (50 mM final concentration), Tris-HCl (30 mM final concentration, pH 8.4), MgCl2 (2 mM final concentration), each of the 4 dNTPs (400 µM final concentration), 10 pmoles of each PCR primer for a 560 bp fragment of the thymidylate synthase gene (Forward: 5'-ATGCTTAGTAGGCAATTCTG-3' (SEQ ID NO: D, Reverse: 5'-TTTGGTTGTCAGCAGAGG-3' (SEQ ID NO: 2), and 2 units of Taq DNA polymerase. 50 ng of purified control human DNA (from saliva, collected and purified using Oragene™) was added as the template. PCR reactions were performed in an Eppendorf Mastercycler™ gradient PCR machine. The total reaction volume was 50 µl. The thermal cycling conditions were the same as in Example 2.

Agarose Gel Electrophoresis

Agarose gel analysis was performed as described in Example 2.

Summary

As can be seen in FIG. 3, 8 mM NaOH was the highest final concentration of NaOH that could be used in a 50 µl conventional PCR reaction without strongly inhibiting the reaction. This is equivalent to a starting concentration of 400 mM NaOH that would then be diluted 1:1 with a saliva sample before being used for PCR.

Example 5

Determination of the Volume of a NaOH/Saliva Mixture that is Non-Inhibitory in a PCR Reaction Method One-ml of saliva was collected from a single donor and mixed with an equal volume of 100 mM sodium hydroxide solution. The sample was vortexed and stored at room temperature. After 7 days of storage at room temperature, aliquots were removed and added to a standard 50 μl PCR reaction. The aliquots ranged in volume from 1 to 20 μl.

PCR Conditions

The PCR conditions were the same as in Example 2. The total reaction volume was kept constant at 50 μl. The thermal cycling conditions were the same as in Example 2.

Agarose Gel Electrophoresis

Agarose gel analysis was performed as described in Example 2.

Summary

Figure 4:
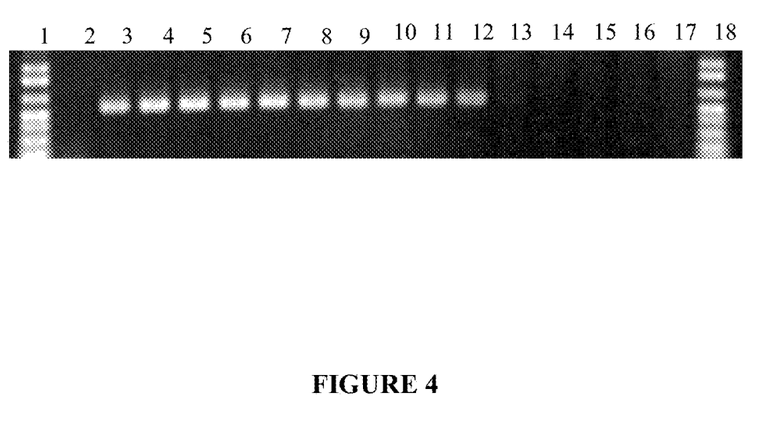
FIG. 4 shows an agarose gel stained with ethidium bromide following electrophoresis of PCR products and depicts the effect of increasing volumes of a NaOH/saliva mixture on a 50 μL PCR amplification reaction. The contents of the lanes in the agarose gel are as follows.

As can be seen in FIG. 4, up to 10 μL of NaOH/saliva mixture could be added to a 50 μl conventional PCR reaction without inhibiting the reaction.

Example 6

Inhibition of a PCR Reaction by Oragene™

Oragene™ (DNA Genotek Inc.) is a saliva collection device that contains an aqueous solution that stabilizes the DNA in saliva at room temperature.

Method 100 mM sodium hydroxide, 100 mM potassium hydroxide, 200 mM sodium carbonate, or Oragene™ DNA-preserving solutions were diluted 1:1 with distilled water and 2 μl of each diluted composition was added to a standard PCR reaction.

PCR Conditions

The PCR conditions were the same as in Example 2. The thermal cycling conditions were the same as in Example 2. Fifty-ng of purified DNA was added to each reaction as the template.

Agarose Gel Electrophoresis

Agarose gel analysis was performed as described in Example 2.

Summary

Figure 5:
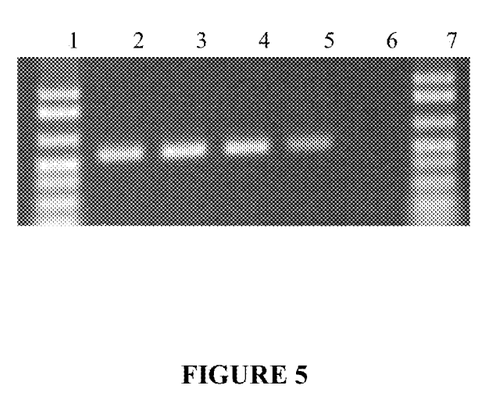
FIG. 5 shows an agarose gel stained with ethidium bromide following electrophoresis of PCR products and depicts the inhibitory effect of Oragene™ compared to other compositions on a PCR amplification reaction. The contents of the lanes in the agarose gel are as follows.

As can be seen in FIG. 5, Oragene™ DNA-preserving solution is inhibitory to PCR. In contrast, this example demonstrates that the sodium hydroxide, potassium hydroxide, and sodium carbonate compositions can be added directly to a PCR reaction without inhibiting the reaction.

Example 7

Improved Extraction of DNA from Saliva

French et al. (French et al. (2002) Molecular and Cellular Probes. 16: 319-326) diluted fresh whole saliva 1:1 with water and used this mixture for quantitative real-time PCR. Diluted saliva samples were either used immediately or stored at 4° C. (2 to 3 days) or −20° C. The calculated concentration of DNA from the sample available for real-time PCR was found to be between 0.1 ng/μl and 3.5 ng/μl, varying between samples obtained from different individuals.

The examples in Tables I, II and III show the compositions of present invention make available significantly more DNA from saliva than a mixture of saliva and water.

Method

One-ml of saliva was collected from a single donor and mixed with 1 ml of 100 mM sodium hydroxide, 100 mM potassium hydroxide, 200 mM sodium carbonate, or distilled water. The mixtures were stored at room temperature. At Day 1 (Table I), Day 14 (Table II), and Day 365 (Table III), 1 μl of each mixture was added directly to a real-time PCR reaction as described below.

Additionally, 1 ml of saliva from the same donor was collected and mixed with a solution of 20 mM CDTA; 400 mM NaOAc (sodium acetate); 200 mM Tris-HCl, 0.05% SDS; pH adjusted to 8.0. Following saliva collection and prior to storage, 20 μl of Proteinase K (1 mg/ml concentration) was added to the mixture (10 μg/mL final concentration). Samples were stored at room temperature. At Day 1, Day 14, and Day 365, 1 μl of this mixture was added directly to a real-time PCR reaction as described below after incubation at 60° C. for 1 hour.

Real-Time PCR Conditions

Real-time PCR reactions were performed in a Rotor-Gene™ 3000 real-time thermal cycler (Corbett Research). The total reaction volume was 25 μl.

Each reaction contained KCl (50 mM final concentration), Tris HCl (20 mM, pH 8.4), $MgCl_2$ (3 mM), each of the 4 dNTPs (400 μM); 5 pmoles of each primer to generate a 143 bp fragment of the human thymidylate synthase gene: (Forward primer: 5'-GCCCTCTGCCAGTTCTA-3' (SEQ ID NO: 3), Reverse primer: 5'-TTCAGGCCCGTGATGT-3' (SEQ ID NO: 4)), 2 units of Taq DNA polmerase, SYBR Green I dye (Molecular Probes), 1:25,000 final concentration.

Thermocycling conditions consisted of: 1 cycle of 96° C. for 5 min; 40 cycles of 95° C. for 20 sec, 55° C. for 20 sec, 72° C. for 30 sec. Melting curve analysis conditions consisted of: 72-97° C.; 45 sec at 72° C., then 5 sec per degree Celsius to 97° C.

A standard curve was constructed using purified DNA of known concentration.

Results

The DNA concentration of the input sample was automatically calculated using the Rotor Gene™ 3000 software with reference to the standard curve.

TABLE I

Real-time PCR results from Day 1

| Composition | Threshold crossing point from real-time PCR (Ct) | Calculated DNA concentration of input sample based on Ct value (ng/μl) |
|---|---|---|
| Control DNA, 30 ng/μL | 21.06 | 26.80 |
| Control DNA, 15 ng/μL | 22.14 | 14.43 |
| Control DNA, 7.5 ng/μL | 23.21 | 7.84 |
| Control DNA, 3.75 ng/μL | 24.06 | 4.84 |
| Control DNA, 1.90 ng/μL | 25.83 | 1.76 |
| Control DNA, 1.00 ng/μL | 26.67 | 1.09 |
| Control DNA, 0.50 ng/μL | 28.31 | 0.43 |
| No template | | 0 |
| Water + saliva | 34.6 | 0.01 |
| CDTA/SDS/NaOAC/Tris + saliva | 23.33 | 7.32 |
| 100 mM sodium hydroxide + saliva | 23.54 | 6.51 |
| 100 mM potassium hydroxide + saliva | 24.96 | 2.89 |
| 200 mM sodium carbonate + saliva | 25.19 | 2.54 |

TABLE II

Real-time PCR results from Day 14

| Composition | Threshold crossing point from real-time PCR (Ct) | Calculated DNA concentration of input sample based on Ct value (ng/μl) |
|---|---|---|
| Control DNA, 30 ng/μL | 20.56 | 25.88 |
| Control DNA, 15 ng/μL | 21.2 | 17.71 |
| Control DNA, 7.5 ng/μL | 22.44 | 8.50 |
| Control DNA, 3.75 ng/μL | 23.97 | 3.45 |

TABLE II-continued

Real-time PCR results from Day 14

| Composition | Threshold crossing point from real-time PCR (Ct) | Calculated DNA concentration of input sample based on Ct value (ng/μL) |
|---|---|---|
| Control DNA, 1.90 ng/μL | 25.07 | 1.80 |
| Control DNA, 1.00 ng/μL | 26.19 | 0.92 |
| Control DNA, 0.50 ng/μL | 27.11 | 0.54 |
| No template | | 0 |
| Water + saliva | 31.81 | 0.03 |
| CDTA/SDS/NaOAC/Tris + saliva | 23.62 | 4.23 |
| 100 mM sodium hydroxide + saliva | 23.01 | 6.06 |
| 100 mM potassium hydroxide + saliva | 24.12 | 3.15 |
| 200 mM sodium carbonate + saliva | 24.02 | 3.35 |

TABLE III

Real-time PCR results from Day 365

| Composition | Threshold crossing point from real-time PCR (Ct) | Calculated DNA concentration of input sample based on Ct value (ng/μL) |
|---|---|---|
| Control DNA, 30 ng/μL | 21.21 | 27.91 |
| Control DNA, 15 ng/μL | 22.11 | 16.32 |
| Control DNA, 7.5 ng/μL | 23.43 | 7.44 |
| Control DNA, 3.75 ng/μL | 24.68 | 3.52 |
| Control DNA, 1.9 ng/μL | 25.5 | 2.15 |
| Control DNA, 1.0 ng/μL | 26.81 | 0.99 |
| Control DNA, 0.5 ng/μL | 28.04 | 0.47 |
| No template | 33.99 | 0.01 |
| Water + saliva | | 0 |
| CDTA/SDS/NaOAc/Tris + saliva | 23.51 | 7.07 |
| 100 mM sodium hydroxide + saliva | 26.06 | 1.54 |
| 100 mM potassium hydroxide + saliva | 26.48 | 1.20 |
| 200 mM sodium carbonate + saliva | 25.35 | 2.35 |

Summary

The purpose of this study was to demonstrate the improved performance of the compositions of the present invention for storing DNA in comparison to the use of water alone for storing DNA. It should be appreciated that the real-time PCR technique used in this study is merely semi-quantitative and, due to the inherent degree of error in this technique, the calculated DNA concentration values may not be the actual DNA concentration. However, as would be readily appreciated by a worker skilled in the art, this method does provide an accurate comparison between the samples tested As can be seen in Tables I, II, and III, there is negligible DNA detectable by real-time PCR when saliva is stored in water for 1, 14, or 365 days. In contrast, the concentrations of DNA in the various compositions of the present invention, range from 2.54 to 7.32 ng/μL at Day 1 (Table I), 3.15 to 6.06 ng/μL at Day 14 (Table II), and 1.20 to 7.07 ng/μL at Day 365 (Table III).

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A method of amplifying deoxyribonucleic acid (DNA) directly from a bodily fluid, comprising:
   (a) mixing a sample of the bodily fluid with an aqueous composition for extracting and preserving nucleic acid from a sample of a bodily fluid such that said nucleic acid within said sample remains stable at room temperature following mixture with said aqueous composition, said aqueous composition comprising:
      (i) a denaturing agent;
      (ii) a chelator;
      (iii) a buffering agent at a pH of about pH 7 to about pH 11; and
      (iv) a protease;
      wherein said aqueous composition does not inhibit a nucleic acid amplification reaction when said composition is added to an amplification reaction mixture at an amount of at least 2% (vol./vol.) of the total volume of said amplification reaction mixture, wherein the final concentration of said denaturing agent in said amplification reaction mixture is less than about 0.01% (wt./vol.), and wherein said nucleic acid is capable of being amplified directly from said sample in said nucleic acid amplification reaction in the absence of an additional detergent; and
   (b) diluting at least 2% (vol./vol.) of the mixture formed in step (a) in an amplification reaction mixture without prior extraction of nucleic acid molecules present in said mixture and subjecting said amplification reaction mixture to polymerase chain reaction (PCR) amplification, wherein said PCR amplifies said nucleic acid molecules.

2. The method of claim 1, wherein the bodily fluid is saliva.

3. The method of claim 1, wherein the mixture formed in step (a) is stored at room temperature for at least fourteen days prior to step (b).

4. The method of claim 1, wherein the mixture formed in step (a) is stored at room temperature for at least three hundred and sixty-five days prior to step (b).

5. The method of claim 1, additionally comprising the step of heating the mixture at a temperature of from about 45° C. to 80° C. for about 15 to 60 minutes prior to step (b).

6. The method of claim 1, wherein said denaturing agent is SDS, said chelator is CDTA, said buffering agent is TrisHCl, and said protease is proteinase K.

7. The method of claim 1, wherein said aqueous composition comprises 0.05% SDS, 20 mM CDTA, 200 mM TrisHCl pH 8.0, 400 mM NaOAc, and 10 μg/ml proteinase K.

8. The method of claim 1, wherein step (b) comprises diluting between 2% (vol.) and 10% (vol.) of the mixture formed in step (a) in said amplification reaction mixture.

9. A method of amplifying deoxyribonucleic acid (DNA) directly from a bodily fluid, comprising:
   (a) obtaining a sample comprising a bodily fluid admixed with a composition comprising:
      (i) a denaturing agent;
      (ii) a chelator;
      (iii) a buffering agent that establishes a pH of said sample of about pH 7 to about pH 11; and
      (iv) a protease wherein said DNA within said sample remain stable at room temperature;
   (b) preparing an amplification reaction mixture comprising at least 2% (vol./vol.) of the sample, wherein said amplification reaction mixture is prepared without prior extraction of said nucleic acid molecules from said sample and the final concentration of said denaturing agent in said amplification reaction mixture is less than about 0.01% (wt./vol.); and
   (c) subjecting said amplification reaction mixture to polymerase chain reaction (PCR) amplification, wherein said PCR amplifies said nucleic acid molecules,
   and wherein said DNA is capable of being amplified in said PCR amplification in the absence of an additional detergent.

10. The method of claim 9, wherein the bodily fluid is saliva.

11. The method of claim 9, wherein the sample is stored at room temperature for at least fourteen days prior to step (b).

12. The method of claim 9, wherein the sample is stored at room temperature for at least three hundred and sixty-five days prior to step (b).

13. The method of claim 9, additionally comprising the step of heating the sample at a temperature of from about 45° C. to 80° C. for about 15 to 60 minutes prior to step (b).

* * * * *